United States Patent [19]

Grollier et al.

[11] Patent Number: 4,842,851

[45] Date of Patent: * Jun. 27, 1989

[54] POLYAMINO AMIDES FOR PROTECTING HAIR AGAINST ATMOSPHERIC ATTACK, AND IN PARTICULAR AGAINST LIGHT, AND PROCESS FOR PROTECTING HAIR EMPLOYING SUCH POLYAMINOAMIDES

[75] Inventors: Jean F. Grollier, Paris; Claude Dubief, Le Chesnay, both of France

[73] Assignee: L'Oreal, Paris, France

[*] Notice: The portion of the term of this patent subsequent to Nov. 3, 2088 has been disclaimed.

[21] Appl. No.: 56,693

[22] Filed: Jun. 2, 1987

[30] Foreign Application Priority Data

Jun. 2, 1986 [LU] Luxembourg .................. 86452

[51] Int. Cl.⁴ .............. A61K 7/11; A61K 7/08; A61K 7/075; A61K 7/42
[52] U.S. Cl. ................................ 424/70; 424/59; 424/78; 424/47; 424/DIG. 2; 424/71
[58] Field of Search ............ 424/70, 59, 78, 47, 424/DIG. 2, 71

[56] References Cited

U.S. PATENT DOCUMENTS

| | | | |
|---|---|---|---|
| 2,961,347 | 11/1960 | Floyd | 428/254 |
| 3,227,615 | 1/1966 | Korden | 132/7 |
| 3,632,559 | 1/1972 | Matter et al. | 525/430 |
| 3,821,372 | 6/1974 | Vanlerberghe et al. | 514/786 |
| 4,172,887 | 10/1979 | Vanlerberghe et al. | 424/70 |
| 4,189,468 | 2/1980 | Vanlerberghe et al. | 424/70 |
| 4,277,581 | 7/1981 | Vanlerberghe et al. | 525/420 |

FOREIGN PATENT DOCUMENTS

| | | |
|---|---|---|
| 1519979 | 2/1968 | France . |
| 1527085 | 4/1968 | France . |
| 2091516 | 1/1972 | France . |
| 2252840 | 6/1975 | France . |
| 2113245 | 8/1983 | United Kingdom . |

Primary Examiner—Ellis P. Robinson
Assistant Examiner—Susan S. Rucker
Attorney, Agent, or Firm—Cushman, Darby & Cushman

[57] ABSTRACT

The invention relates to the finding that various polyaminoamide polymers function to protect the hair from deterioration due to atmospheric attack, particularly by light, thereby preserving the mechanical properties of the hair. The polyaminoamide polymers are known and include those polyaminoamide polymers described in U.S. Pat. Nos. 2,961,347, 3,227,615, 4,172,887, 4,189,468 and 4,277,581 and French Pat. No. 1,583,363.

14 Claims, No Drawings

POLYAMINO AMIDES FOR PROTECTING HAIR AGAINST ATMOSPHERIC ATTACK, AND IN PARTICULAR AGAINST LIGHT, AND PROCESS FOR PROTECTING HAIR EMPLOYING SUCH POLYAMINOAMIDES

The present invention relates to the use of polyaminoamides as agents for protecting hair keratin against atmospheric attack and in particular light, and a process for protecting hair against atmospheric attack, and in particular against light.

It has been known for a long time that light attacks the keratin in hair and in the skin. Many publications disclose that natural light destroys certain amino acids in hair and that, by modifying the hair fibre, it decreases its mechanical properties; a decrease in the mechanical properties is understood to mean chiefly the decrease in the plateau at 15% elongation and in the breaking load.

The plateau at 15% elongation is the weight which must be applied to a wet hair of a given length in order to elongate it by 15%. The higher the weight, the more elastic and the stronger is the hair.

The breaking load is the weight which must be applied to a wet hair, of a given length, in order to break it.

In order to combat the attack on hair keratin due to light, it has already been proposed to employ substances capable of filtering luminous radiations. In particular, filtering agents which are well known in the art have been tried, such as benzophenone derivatives, for example 2-hydroxy-4-methoxybenzophenone, or else dibenzoylmethane derivatives, for example 4-tert-butyl-4'-methoxydibenzoylmethane.

However, these filtering substances have not been found effective in preserving the mechanical properties of hair, namely its elasticity and its wet strength, against the harmful effects of light.

On the contrary, it has become apparent that their presence in certain cosmetic compositions could even accentuate the deterioration in mechanical properties, particularly the decrease in the plateau at 15% elongation and in the breaking load.

The applicants have now surprisingly found that certain polymers belonging to the group of polyaminoamides were capable of preserving the mechanical properties of hair against damage by light. It has been possible to demonstrate this property by exposure to natural light (sunny environment) and to artificial light (xenon lamp of an accelerated aging apparatus of the Suntest Hanau type).

The present invention relates, therefore, to the use of certain classes of polyaminoamides as agents for protecting the mechanical properties of hair and essentially the plateau at 15% elongation and the breaking load against the degradation caused by atmospheric attacks, and especially by light.

The polyaminoamides employed in accordance with the present invention are polymers which are known per se and which belong to the following four classes:

I. The polyaminoamides (A) prepared by polycondensation of an acidic compound chosen from (a) dicarboxylic organic acids, (b) double-bonded aliphatic monoand dicarboxylic acids, (c) esters of the abovementioned acids, preferably the esters of lower alkanols containing 1 to 6 carbon atoms, (d) mixtures of these compounds with a polyamine chosen from mono- or bis-secondary bis-primary polyalkylenepolyamides, it being possible for 0 to 40 mol % of this polyamine to be replaced by a bis-primary amine, preferably ethylenediamine, or by a bis-secondary amine, preferably piperazine, and it being possible for 0 to 20 mol % to be replaced by hexamethylenediamine.

The polyaminoamides (A) may be crosslinked by means of a crosslinking agent (B) chosen from epihalohydrins, diepoxides, dianhydrides, unsaturated anhydrides and bis-unsaturated derivatives, employed in proportions of 0.025 to 0.35 mole per secondary amine group of the polyaminoamide (A).

The crosslinked polyaminoamides may also be alkylated with an epoxide such as glycidol, ethylene oxide, propylene oxide, trimethylepoxypropylammonium chloride or with an unsaturated derivative such as acrylamide.

The crosslinked, alkylated if desired, polyaminoamides (A) are completely soluble in water at a concentration of 10% without forming a gel; the viscosity of a polymer solution at a concentration of 10% in water at 25° C. is higher than 0.003 Pa s. They do not retain reactive groups, have no alkylating properties and are chemically stable.

These polymers and their preparation are described in greater detail in U.S. Pat. No. 4,172,887.

II. The water-soluble crosslinked polyaminoamides obtained by crosslinking a polyaminoamide (A) as defined above by means of a crosslinking agent chosen from the group consisting of:

II.1. the simple difunctional compounds chosen from the group consisting of (1) bishalohydrins, (2) bisazetidiniums, (3) bishaloacyldiamines and (4) alkyl bishalides;

II.2. the oligomers obtained by reaction of a compound (a) chosen from the group consisting of (1) bishalohydrins, (2) bisazetidiniums, (3) bishaloacyldiamines, (4) alkyl bishalides, (5) epihalohydrins, (6) diepoxides and (7) bis-unsaturated derivatives with a compound (b) which is a difunctional compound reactive towards the compound (a);

II.3. the product of quaternization of a compound chosen from the group consisting of the compounds II.1. and the oligomers II.2. and containing one or more tertiary amine groups capable of being completely or partially alkylated with an alkylating agent (c) chosen from the group consisting of methyl or ethyl chlorides, bromides, iodides, sulphates, mesylates and tosylates, benzyl chloride or bromide, ethylene oxide, propylene oxide and glycidol;

the crosslinking being carried out by means of 0.025 to 0.35 mole, in particular 0.025 to 0.2 mole and more particularly 0.025 to 0.1 mole, of crosslinking agent per amine group of the polyaminoamide.

These crosslinking agents and these polymers, as well as the process for preparing them, are described in U.S. Pat. Nos. 4,189,468 and 4,277,581.

III. The water-soluble polyaminoamide derivatives resulting from the condensation of a polyalkylenepolyamine containing two primary amino groups, at least one secondary amino group and alkylene groups containing 2 to 4 carbon atoms with a dicarboxylic acid of formula:

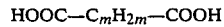

$$HOOC-C_mH_{2m}-COOH$$

in which m denotes an integer from 4 to 8, or with a functional derivative of an acid of this kind, in a molar ratio of 0.8:1 to 1.2:1, which condensation is followed by an alkylation in aqueous solution with difunctional alkylating agents corresponding to the formula:

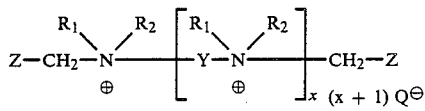

in which
x denotes an integer from 0 to 7,
Z denotes one of the following groups:

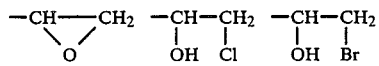

$R_1$ and $R_2$ each denote a lower alkyl group or a lower hydroxyalkyl group containing 1 to 4 carbon atoms,
Y denotes an alkylene radical containing 2 to 6 carbon atoms, a 2-hydroxy-1,3-propylene radical or one of the following two radicals:

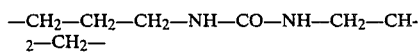

Q denotes halogen, sulphate or methosulphate,
the quantity of difunctional alkylating agent being chosen so that the alkylation product still remains in solution.

As polyaminoamides of this type, there may be mentioned, for example, the adipic acid-dialkylaminohydroxyalkyl-dialkylenetriamine polymers in which the alkyl radical contains 1 to 4 carbon atoms and preferably denotes methyl, ethyl or propyl, which are described in U.S. Pat. No. 3,632,559.

Compounds which permit particularly advantageous results to be obtained are the adipic acid-dimethylaminohydroxypropyl-diethylenetriamine polymers sold by Sandoz under the trade names "Cartaretine F, F4 or F3".

IV. The water-soluble polymers obtained by reaction of a polyalkylenepolyamine containing two primary amine groups and at least one secondary amine group with a dicarboxylic acid chosen from diglycolic acid and saturated aliphatic dicarboxylic acids containing 3 to 8 carbon atoms, the molar ratio of the polyalkylenepolyamine to the dicarboxylic acid being between 0.8:1 and 1.4:1; the resultant polyamide being made to react with epichlorohydrin in a molar ratio of epichlorohydrin to the secondary amine group of the polyamide of between 0.5:1 and 1.8:1, which polymers are described in U.S. Pat. Nos. 3,227,615 and 2,961,347.

Polymers which are of particular interest are those sold by Hercules Incorporated under the trade name "Hercosett 57" or by Hercules Incorporated under the trade name "PD 170" (copolymer of adipic acid with diethylenetriamine, crosslinked with dpichlorohydrin) and "Delsette 101" (adipic acid-epoxypropyl-diethylenetriamine copolymer).

According to the present invention, the polyaminoamides I to IV as defined above are employed to preserve the mechanical properties of hair from attack by light, in quantities of between 0.1 and 8% by weight, and preferably between 0.2 and 3.5% by weight, in a cosmetically acceptable medium.

The polyaminoamides I to IV according to the invention may be employed to protect natural or sensitized hair. "Sensitized hair" means hair which has undergone a permanent-waving, dyeing or bleaching treatment.

The cosmetic compositions for hair which are used in accordance with the invention to protect it against degradation by light and containing the polyaminoamides I to IV as defined above as active compounds may be presented in the form of aqueous or aqueous-alcoholic solutions or dispersions (the alcohol being in most cases a lower alkanol such as ethanol or isopropanol), which are thickened or unthickened, oily compositions, creams, gels, aerosol foams or sprays and may contain the adjuvants which are usually employed in hair compositions adapted to the intended application.

These compositions may, or may not, be followed by a rinse and may constitute shampoos, after-shampoos, products for rinsing for applying before or after a shampoo, before or after dyeing or bleaching, before or after permanent-waving or hair-straightening, unrinsed compositions such as lotions, gels, creams, sprays or foams for hair setting, for blow-drying, and restructuring compositions.

When the cosmetic compositions employed according to the invention are compositions which are not followed by a rinsing, the polyaminoamide, as an active agent preserving the mechanical properties of hair against light, is present in a proportion of 0.1 to 5% by weight based on the total weight of the composition, and preferably in a proportion of 0.2 to 2% by weight.

When the cosmetic compositions employed according to the invention are compositions followed by a rinsing, the polyaminoamide is present in a proportion of 0.1 to 8% by weight, and preferably of 0.5 to 3.5% by weight, based on the total weight of the composition.

The cosmetic compositions for hair according to the invention have a pH of between 2 and 11 and preferably between 3 and 9.

The cosmetic compositions employed according to the invention may also contain cosmetic agents which are well known in the art, provided that they do not themselves alter the mechanical properties of the hair keratin.

The adjuvants or cosmetic agents which are generally present in the cosmetic compositions employed according to the invention are, for example, cationic, anionic, amphoteric or nonionic surface agents or their mixtures, thickeners, polymers other than polyaminoamides I to IV, softeners, preservatives, foam-stabilizers, electrolytes, oils, pH regulating agents, waxes, antigrease agents, sequestering agents, perfumes, colorants, synergists and organic solvents.

The cationic, anionic, nonionic or amphoteric surface-active agents or their mixtures are generally employed in proportions of 0.1 to 70% by weight and preferably of 0.5 to 50% by weight based on the total weight of the composition.

When the cosmetic compositions for hair which are employed according to the invention are shampoos, the latter are essentially characterized in that, in addition to the polyaminoamide as defined above, they contain at least one anionic, nonionic, cationic or amphoteric surface agent or a mixture of such surface agents, in an aqueous or oily medium. The shampoos may also contain various adjuvants such as colorants, preservatives, thickeners, foam-stabilizers, synergists, softeners, electrolytes, sequestrants, one or more cosmetic resins, perfumes, natural essences, oils, as well as any other adjuvant usually employed in a shampoo. The concentration of surface agent in these shampoos is generally between 2 and 50% by weight. Their pH is generally between 3 and 9.

When the compositions employed according to the invention are compositions which are not rinsed - lotion, cream, gel, foam or spray for blow-drying, for hair setting, for dressing or treating the hair - then in addition to the polyaminoamide as defined above they generally comprise, in an aqueous or aqueous-alcoholic medium, at least one cationic, anionic, nonionic or amphoteric polymer or a mixture of such polymers in quantities which are generally between 0.1 and 10% and preferably between 0.1 and 3% by weight, and, if desired, foam-suppressors.

When the hair compositions according to the invention are rinsed lotions, which are also called a "rinse", they are applied before or after dyeing or bleaching, before or after permanent-waving, before or after shampooing or between two stages of shampooing, and are then rinsed off after a period of being left in place.

These compositions may be aqueous or aqueous-alcoholic solutions which contain surfactants, if desired; they may also be emulsions or gels. These compositions may also be pressurized in an aerosol in the form of sprays or foams.

In these rinsed compositions, the concentration of surface-active agents may vary between 0.1 and 10%, and preferably between 0.5 and 7% by weight. They may also contain nonionic, cationic, anionic or amphoteric polymers.

When the hair compositions are in the form of gels, to be rinsed or not, they contain thickeners in the presence or absence of solvents.

The thickeners may be sodium alginate, gum arabic or xanthane gum or cellulose derivatives such as methyl cellulose, hydroxymethyl cellulose, hydroxyethyl cellulose, hydroxypropyl cellulose, carboxymethyl cellulose or carboxylic polymers such as the "Carbopols". Thickening of the lotions may also be produced by means of a mixture of polyethylene glycol and polyethylene glycol stearate or distearate or by means of a mixture of phosphoric esters and amides. The concentration of thickener may vary from 0.1 to 30%, and preferably from 0.2 to 15% by weight.

The pH of rinsed lotions may vary between 2 and 10 and is preferably between 3 and 8.

When the hair compositions of the invention are restructuring lotions, they contain products which strengthen the keratin chain of hair. This class of products includes the methylolated derivatives such as those described in French Pat. Nos. 1,527,085 and 1,519,979.

The cosmetic compositions for hair which are employed according to the invention and which are to be applied to sensitized hair advantageously contain an electrolyte.

The presence of the electrolyte in the composition reduces or eliminates the tendency, exhibited by sensitized hair, to fix the polymers permanently. The electrolytes employed are water-soluble alkali metal or alkaline-earth metal salts of inorganic or organic acids, and preferably sodium, potassium, ammonium and calcium chlorides and acetates. The quantity of electrolyte is preferably between 0.01 and 5% by weight, advantageously between 0.4 and 3% by weight, based on the total weight of the composition.

The present invention also provides a process for protecting hair keratin against atmospheric attacks, and in particular against light, consisting in applying to the hair an effective quantity of at least one polyaminoamide belonging to classes (I) to (IV) as defined above, in a cosmetically acceptable medium.

The examples which follow illustrate the invention without, however, limiting it.

Examples 1 to 3 illustrate the use of polyaminoamides defined according to the invention as agents for protecting the mechanical properties of hair against the degradation due to light.

EXAMPLE 1

Hanks of bleached hair were exposed to natural light for 130 hours. The hair was then immersed in softened water at 20° C. overnight and then the load and the elongation at break were measured on a Lhomargy DY 11 tensometer, together with the plateau at 15% elongation, both for exposed and for control, that is to say unexposed, hair, the tensile measurements being made in water at 20° C.

In this way it was possible to record a loss of 8% in this plateau at 15% elongation and a loss of 11% in the breaking load in the case of hair which had been subjected to an extended exposure to natural light, when compared with the unexposed hair controls.

Hanks of bleached hair were then treated with an aqueous solution containing 3% by weight of polyaminoamide prepared according to Example Ia of French Pat. No. 2,252,840: polycondensate of adipic acid with diethylenetriamine, crosslinked with epichlorohydrin in a proportion of 11 moles of epichlorohydrin per 100 secondary amine groups of the polyaminoamide.

After being rinsed, rough-dried and dried, the hair was immersed in softened water at 20° C. overnight and then the parameters described above were measured under the same conditions, and a loss of only 4% was observed in the breaking load and in the plateau at 15% elongation, compared with the unexposed hank controls.

The protective effect of the polyamide on the hair fibre, against light, has therefore been demonstrated by measuring the decrease in the deterioration of the mechanical properties of the fibre subjected to an extended exposure to natural light.

EXAMPLE 2

Using the same tensometer, the parameters described in Example 1 were measured in the case of hanks of bleached hair which had been subjected to a "sun test" lasting for 5×24h, with the aid of a "Suntest Hanau" apparatus. This apparatus consists of a xenon lamp and a system of filters producing a radiation which, to a very large extent, corresponds to solar radiation. The energetic radiation is approximately 585 W/m$^2$ in the region of wavelengths between 300 and 830 nm (total radiation).

When compared with bleached hank controls, the hanks which have been subjected to a "sun test" show a loss of 11% in the plateau at 15% elongation and 10% in the breaking load. On the other hand, bleached hanks treated with an aqueous solution containing 3% of polyaminoamide prepared according to Example Ia of Patent 2,252,840, and then rinsed, rough-dried and dried, show only a loss of 3% in the plateau at 15% elongation and 6% in the breaking load.

EXAMPLE 3

In an identical manner to Example 1, bleached hanks treated with an aqueous solution containing 3% of the polyaminoamide prepared according to French Pat. No. 2,252,840 by alkylation of the compound prepared in Example Ia with the aid of trimethylepoxypropylammonium chloride, and then rinsed, rough-dried and dried, show only a loss of 4% in this plateau at 15% elongation and 3% in the breaking load.

Examples 4 to 8, which follow, illustrate cosmetic compositions which protect hair against atmospheric attacks and especially against light.

EXAMPLE 4

A shampoo with the following composition is prepared:

Polyaminoamide prepared according to Example Ia of French Pat. No. 2,252,840:

| | | |
|---|---|---|
| polycondensate of adipic acid with diethylenetriamine, crosslinked with epichlorhydrin in a proportion of 11 moles of epichlorhydrin per 100 secondary amine groups of the polyaminoamide | 2.5 g (active substance) | AS |
| Sodium alkyl ($C_{12}$–$C_{14}$) ether sulphate, oxyethylenated with 2.2 moles of ethylene oxide | 7 g | AS |
| Cocamidopropylbetaine sold at a concentration of 30% of AS by Goldschmidt under the trade name "Tego-Betain" | 5 g | AS |
| HCl q.s. pH: 8.1 | | |
| Perfume, preservative q.s. | | |
| Water q.s. | 100 g | |

EXAMPLE 5

A shampoo with the following composition is prepared:

Polyaminoamide prepared according to Example Ia of French Pat. No. 2,252,840:

| | | |
|---|---|---|
| polycondensate of adipic acid with diethylenetriamine, crosslinked with epichlorhydrin in a proportion of 11 moles of epichlorhydrin per 100 secondary amine groups of the polyaminoamide | 3.5 g | AS |
| Laureth-5 carboxylic acid sold in a concentration of 90% AS by Chem-Y under the trade name "Akypo RLM 45" | 12 g | AS |
| Copra fatty acids diethanolamide sold by Henkel under the trade name "Comperlan KD" | 2 g | |
| HCl q.s. pH: 7 | | |
| Perfume, preservative q.s. | | |
| Water q.s. | 100 g | |

EXAMPLE 6

The blow-drying lotion with the following composition is prepared:

Polyaminoamide prepared according to Example Ia of French Pat. No. 2,252,840:

| | | | |
|---|---|---|---|
| polycondensate of adipic acid with diethylenetriamine, crosslinked with epichlorhydrin in a proportion of 11 moles of epichlorhydrin per 100 secondary amine groups of the polyaminoamide | 0.5 g | | AS |
| Quaternary polyvinylpyrrolidone copolymer with a MW of 100,000, marketed by General Aniline under the trade name "Gafquat 734" at 50% AS | 0.5 g | | AS |
| Ethyl alcohol | q.s. | | 10° |
| Perfume, preservative | q.s. | | |
| Lactic acid | q.s. | pH: 7.5 | |
| Water | q.s. | | 100 g |

EXAMPLE 7

The hair setting lotion with the following composition is prepared:

Polyaminoamide prepared according to Example Ia of French Pat. No. 2,252,840:

| | | | |
|---|---|---|---|
| polycondensate of adipic acid with diethylenetriamine, crosslinked with epichlorohydrin in a proportion of 11 moles of epichlorohydrin per 100 secondary amine groups of the polyaminoamide | 1.5 g | | AS |
| Polyvinylpyrrolidone | | | 1 g |
| Perfume, preservative | q.s. | | |
| Lactic acid | q.s. | pH: 7.5 | |
| Water | q.s. | | 100 g |

EXAMPLE 8

The blow-drying lotion with the following composition is prepared:

Polyaminoamide prepared according to Example Ia of French Pat. No. 2,252,840:

| | | | |
|---|---|---|---|
| polycondensate of adipic acid with diethylenetriamine, crosslinked with epichlorohydrin in a proportion of 11 moles of epichlorohydrin per 100 secondary amine groups of the polyaminoamide | 0.5 g | | AS |
| Hydroxyethyl cellulose sold by Hercules under the trade name "Natrosol 250 HHR" | 0.8 g | | |
| Lactic acid | q.s. pH: 7.5 | | |
| Perfume, preservative, | colorants q.s. | | |
| Water | q.s. | | 100 g |

EXAMPLE 9

A foaming oil which is applied to hair for a few minutes and which is rinsed off, with the following composition, is prepared:

| | | |
|---|---|---|
| Cartaretine F4 from Sandoz (adipic acid-dimethylamino-hydroxypropyl-diethylenetriamine polymer) | 3 g | AS |
| Mixture of a monoisopropanolamine salt of lauryl ether sulphate, of nonionic, and of diethanolamides of copra fatty acids sold by Henkel under the trade name "Texapon WW 99" | 35 g | |
| Liquid paraffin | 30 g | |
| Perfume preservative q.s. | | |
| Rapeseed oil q.s. | 100 g | |

EXAMPLE 10

A rinsing gel with the following composition is prepared:

| | |
|---|---|
| Xanthane gum sold by Kelco under the | 1 g |

-continued

| | | |
|---|---|---|
| trade name "Keltrol T" | | |
| Sodium chloride | 4 g | |
| Cartaretine F4 from Sandoz | 4 g | AS |
| Sodium alkyl (C₁₀ to C₁₆) ethoxy (30E) carboxylate sold by Marchon under the trade name "Empilan 2747-30" | 1 g | AS |
| HCl q.s. pH: 4.8 | | |
| Perfume, preservative, q.s. | | |
| Water q.s. | 100 g | |

EXAMPLE 11

A shampoo with the following composition is prepared:

| | |
|---|---|
| Hercosett 57 from Hercules Inc. (co-polymer of adipic acid with diethylene-triamine, crosslinked with epichlorohydrin) | 8 g |
| Nonionic surfactant obtained according to French Patent 2,091,516 by condensation of 3.5 moles of glycidol with a C₁₁₋₁₄ α-diol | 12 g |
| HCl q.s. pH: 3 | |
| Perfume, preservative, q.s. | |
| Water q.s. | 100 g |

EXAMPLE 12

A rinsing emulsion with the following composition is prepared:

| | | |
|---|---|---|
| Hydroxyethyl cellulose sold by Hercules under the trade name "Natrosol 250 HHR" | 1.2 g | |
| Mixture of cetostearyl alcohol and of cetostearyl alcohol oxyethylenated with 33 moles of ethylene oxide, sold by Henkel under the trade-name "Sinnowax AO" | 2 g | |
| Stearyl alcohol | 1 g | |
| Cetyl alcohol | 1 g | |
| "Delsette 101" from Hercules Inc. (adipic acid-epoxypropyldiethylenetriamine copolymer) | 1 g | |
| Triethanolamine | q.s. | pH: 8 |
| Perfume, preservative, | q.s. | |
| Water | q.s. | 100 g |

EXAMPLE 13

A rinsing foam with the following composition is prepared:
Polyaminoamide prepared according to Example Ia of French Pat. No. 2,252,840:

| | | |
|---|---|---|
| Polycondensate of adipic acid with diethylenetriamine, crosslinked with epichlorohydrin in a proportion of 11 moles of epichlorohydrin per 100 secondary amine groups of the polyaminoamide | 3 g | AS |
| Polyvinyl alcohol sold by Hoechst under the trade name "Mowiol 40/88" | 1 g | |
| Perfume, preservative, | q.s. | |
| HCl | q.s. | pH: 7 |
| Water | q.s. | 100 g |

The aerosol packaging is produced as follows:

| | |
|---|---|
| above composition: | 90 g |
| "Freons 114/12" (43/57 by weight) sold by Dupont de Nemours | 10 g<br>100 g |

We claim:

1. A process for protecting hair keratin against light comprising applying to hair an effective quantity to protect said hair keratin against light of a cosmetic composition containing, in a cosmetically acceptable medium, at least one polyaminoamide selected from the group consisting of (I) a polyaminoamide (A) prepared by polycondensation of an acidic compound selected from the group consisting of (a) an organic dicarboxylic acid, (b) a double bonded aliphatic mono- or dicarboxylic acid, (c) an ester of the acid defined in (a) and (b), and (d) a mixture of the compounds defined in (a), (b) and (c), with a polyamine chosen from a mono- or bis-secondary bis-primary polyalkylenepolyamine, it being possible for 0 to 40 mol % of said polyalkylene polyamine being replaceable by a bis-primary amine or by a bis-secondary amine and it further being possible for 0 to 20 mol % of said polyalkylene polyamine being replaceable by hexamethylenediamine;

(II) said polyaminoamide (A) of (I) crosslinked with a crosslinking agent selected from the group consisting of an epihalohydrin, a diepoxide, a dianhydride, an unsaturated anhydride and a bis-unsaturated derivative, said crosslinking agent being employed in an amount of 0.025 to 0.35 mole of crosslinking agent per secondary amine group of said polyaminoamide (A);

(III) said crosslinked polyaminoamide (A) of (II) alkylated with an epoxide or an unsaturated derivative;

(IV) a water-soluble crosslinked polyaminoamide obtained by crosslinking said polyaminoamide (A) defined in I above, with a crosslinking agent selected from the group consisting of:

(1) a simple difunctional compound selected from the group consisting of (a) bishalohydrin, (b) a bisazetidinium, (c) a bishaloacyldiamine and (d) an alkyl bishalide;

(2) an oligomer obtained by reaction of a compound (a) selected from the group consisting of (i) a bishalohydrin, (ii) a bisazetidinium, (iii) a bishaloacyldiamine, (iv) an alkyl bishalide, (v) an epihalohydrin, (vi) a diepoxide and (vii) a bis-unsaturated derivative with a compound (b) which is a difunctional compound reactive towards said compound (a);

(3) the quaternization product of a compound selected from the group consisting of said compound (1) and said oligomer (2) and containing one or more tertiary amine groups capable of being completely or partially alkylated with an alkylating agent (c) selected from the group consisting of methyl or ethyl chloride, bromide, iodide, sulphate, mesylate and tosylate, benzyl chloride or bromide, ethylene oxide, propylene oxide and glycidol;

the crosslinking being carried out by means of 0.025 and 0.35 mole of crosslinking agent per amine group of said polyaminoamide;

(V) a water-soluble polyaminoamide derivative resulting from the condensation of a polyalkylene polyamine containing two primary amino groups, at least one secondary amino group and alkylene groups containing 2 to 4 carbon atoms with a dicarboxylic acid having the formula:

HOOC—C$_m$H$_{2m}$—COOH in which m denotes an integer from 4 to 8, or with a functional derivative of said dicarboxylic acid, in a molar ratio of 0.8:1 to 1.2:1, followed by an alkylation in aqueous solution with a difunctional agent having the formula

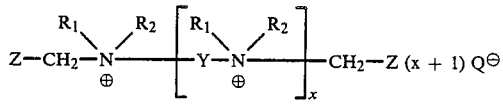

in which
x denotes an integer from 0 to 7,
Z denotes one of

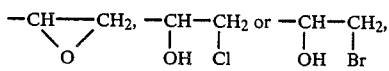

R$_1$ and R$_2$ each denote a lower alkyl group or a lower hydroxyalkyl group containing 1 to 4 carbon atoms, Y denotes an alkylene radical containing from 2 to 6 carbon atoms, a 2-hydroxy-1,3-propylene radical or one of —CH$_2$—CH$_2$—NH—CO—NH—CH$_2$—CH$_2$—and
—CH$_2$—Ch$_2$—CH$_2$—NH—CO—NH—CH$_2$—CH$_2$—CH$_2$—, Q$^\ominus$ denotes halogen, sulphate or methosulphate, the quantity of said difunctional alkylating agent being chosen so that the alkylation product remains in solution; and (VI) a water-soluble polymer obtained by reaction of a polyalkylenepolyamine containing two primary amine groups and at least one secondary amine group with a dicarboxylic acid selected from diglycolic acid and a saturated aliphatic dicarboxylic acid containing 3 to 8 carbon atoms; the molar ratio of said polyalkylenepolyamine to said dicarboxylic acid being between 0.8:1 and 1.4:1; the resultant polyamide being reacted with epichlorohydrin in a molar ratio of epichlorohydrin to the secondary amine group of the said polyamide of between 0.5:1 and 1.8:1.

2. The process of claim 1 wherein said polyaminoamide is a polycondensate of adipic acid with diethylenetriamine, crosslinked with epichlorohydrin in a proportion of 11 moles of epichlorohydrin per 100 secondary amine groups of the said polyaminoamide.

3. The process of claim 1 wherein said polyaminoamide is a polycondensate of adipic acid with diethylenetriamine, crosslinked with epichlorohydrin in a proportion of 11 moles of epichlorohydrin per hundred secondary amine groups of said polyaminoamide and alkylated by means of trimethylepoxypropylammonium chloride.

4. The process of claim 1 wherein said polyaminoamide is an adipic acid-dialkylaminohydroxyalkyl-dialkylenetriamine polymer in which the alkyl radical contains from 1 to 4 carbon atoms.

5. The process of claim 1 wherein said polyaminoamide is a copolymer of adipic acid with diethylenetriamine, crosslinked with epichlorohydrin, or an adipic acid-epoxypropyl-diethylene-triamine copolymer.

6. The process of claim 1 wherein said cosmetic composition is provided in the form of an aqueous or aqueous-alcoholic solution or dispersion, an oily composition, a cream, a gel, an aerosol foam or a spray.

7. The process of claim 1 wherein said cosmetic composition additionally contains at least one adjuvant selected from the group consisting of a surface-active agent, a thickener, a polymer other than said polyaminoamide, a softener, a preservative, a foam stabilizer, an electrolyte, an organic solvent, a silicone derivative, an oil, a wax, an antigrease agent, a pH control agent, a colorant, a perfume and a sequestering agent.

8. The process of claim 1, wherein said cosmetic composition is in the form of a shampoo and contains, in addition to said polyaminoamide, in an aqueous or oily medium, an anionic, cationic, nonionic or amphoteric surface-active agent or a mixture of said surface-active agents, in an amount ranging from 2 and 50 weight percent.

9. The process of claim 1 wherein said cosmetic composition is in the form of a non-rinsed lotion, gel, cream, spray or foam, said cosmetic composition containing, in an aqueous or aqueous-alcoholic medium, in addition to said polyaminoamide present in an amount ranging from 0.1 to 5 weight percent, a cationic, anionic, nonionic or amphoteric polymer or a mixture thereof, present in an amount ranging from 0.1 to 10 weight percent.

10. The process of claim 1 wherein said cosmetic composition is in the form of a rinse lotion, emulsion, gel, foam or spray, containing in an aqueous or aqueous-alcoholic medium, in addition to said polyaminoamide present in an amount ranging from 0.1 to 8 weight percent, a nonionic, cationic, anionic or amphoteric polymer present in an amount ranging from 0.1 to 10 weight percent.

11. The process of claim 1, wherein said cosmetic composition, in the form of a gel, contains in addition to said polyaminoamide, 0.1 to 30 weight percent of a thickener, in the present or not of a solvent.

12. The process of claim 1 wherein said cosmetic composition contains 0.1 to 8 weight percent of said polyaminoamide.

13. The process of claim 1 wherein said cosmetic composition contains 0.2 to 3.5 weight percent of said polyaminoamide.

14. The process of claim 1 wherein said polyaminoamide is a polymer of adipic acid and dimethylaminohydroxypropyl diethylene triamine.

* * * * *

UNITED STATES PATENT AND TRADEMARK OFFICE
CERTIFICATE OF CORRECTION

PATENT NO. : 4,842,851
DATED : Jun. 27, 1989
INVENTOR(S) : GROLLIER et al.

It is certified that error appears in the above-identified patent and that said Letters Patent is hereby corrected as shown below:

On the title page:

delete "[*] Notice: The portion of the term of this patent subsequent to Jul. 4, 2006 has been disclaimed."

Signed and Sealed this

Ninth Day of April, 1991

Attest:

HARRY F. MANBECK, JR.

*Attesting Officer*   *Commissioner of Patents and Trademarks*